United States Patent [19]

Felix

[11] Patent Number: 4,589,907
[45] Date of Patent: May 20, 1986

[54] AMIDOMETHYL ESTER HERBICIDES

[75] Inventor: Raymond A. Felix, Richmond, Calif.

[73] Assignee: Stauffer Chemical Company, Westport, Conn.

[21] Appl. No.: 776,931

[22] Filed: Sep. 17, 1985

[51] Int. Cl.$^4$ ............ A01N 57/18; A01N 39/04
[52] U.S. Cl. ............................ 71/86; 71/94;
71/105; 71/108; 71/110; 71/111; 71/115;
71/116; 558/390; 260/501.15; 546/291;
546/302; 560/21; 560/62; 562/435; 562/472; 558/390
[58] Field of Search ............ 260/465 D, 501.15;
560/21, 62; 546/291, 302; 562/435, 472; 71/94,
105, 108, 110, 111, 115, 116, 86

[56] References Cited

U.S. PATENT DOCUMENTS

| | | | |
|---|---|---|---|
| 4,070,178 | 1/1978 | Johnson et al. | 71/105 |
| 4,175,947 | 11/1979 | Koch et al. | 71/88 |
| 4,309,210 | 1/1982 | Quadranti et al. | 71/93 |
| 4,309,562 | 1/1982 | Takahashi et al. | 71/108 |
| 4,332,960 | 6/1982 | Trösken et al. | 560/62 |
| 4,350,522 | 9/1982 | Bayer et al. | 71/111 |
| 4,400,530 | 8/1983 | Grove | 560/21 |
| 4,401,459 | 8/1983 | Satomi et al. | 71/94 |

Primary Examiner—Dolph H. Torrence
Attorney, Agent, or Firm—Joel G. Ackerman

[57] ABSTRACT

Compounds having the formula

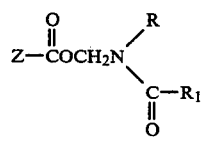

in which Z is

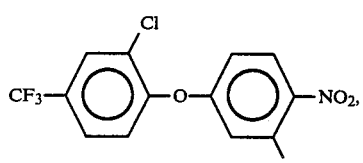

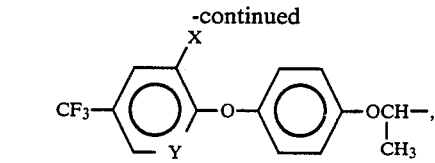

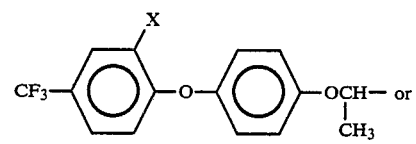

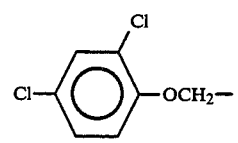

wherein X is hydrogen or halogen and Y is —CH or N; R is alkyl, phenyl, trihalomethylphenyl, cyanomethyl, carboalkoxymethyl,

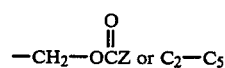

alkenyl; and $R_1$ is hydrogen, lower alkyl, halo-(lower alkyl), or Z; and intermediate alkyl onium salts of the type

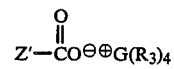

in which $R_3$ is $C_1$–$C_8$ alkyl, G is nitrogen or phosphorus and Z' is

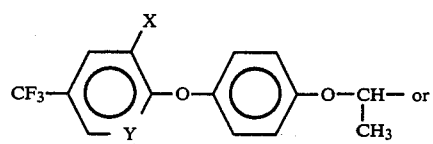

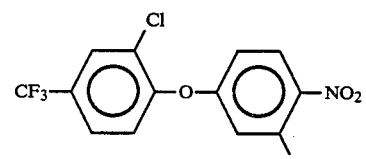

wherein X is hydrogen or halogen and Y is —CH or N; are herbicides.

32 Claims, No Drawings

AMIDOMETHYL ESTER HERBICIDES

This invention relates to novel herbicidal compounds having the formula

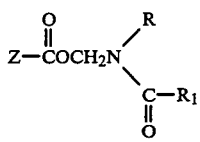

in which Z is

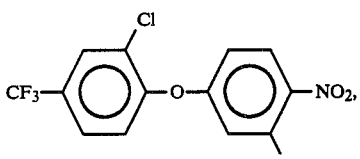

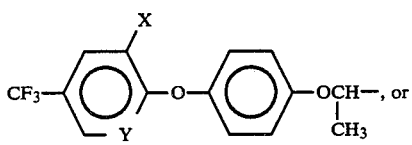

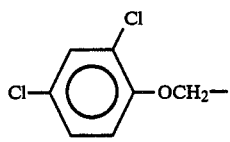

wherein X is hydrogen or halogen and Y is —CH or N; R is alkyl, phenyl, trihalomethylphenyl, cyanomethyl, carboalkoxymethyl,

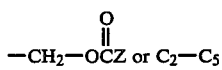

alkenyl; and $R_1$ is hydrogen, lower alkyl, halo-(lower alkyl), or Z; and intermediate alkyl onium salts of the type

in which $R_3$ is $C_1$–$C_8$ alkyl, G is nitrogen or phosphorus, and Z' is

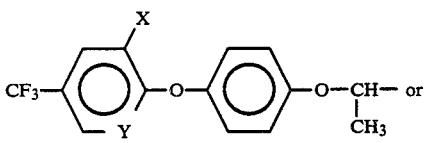

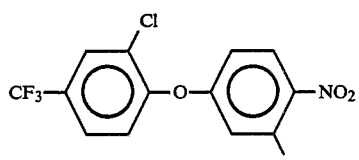

wherein X is hydrogen or halogen and Y is —CH or N.

The terms "alkyl" and "lower alkyl" include both straight and branched chain saturated acyclic hydrocarbyl moieties. The term "alkyl" generally includes such moieties having from 1 to 12 carbon atoms, preferably from 1 to 8, most preferably from 1 to 6. The term "lower alkyl" refers to such groups having from 1 to 6 carbon atoms, preferably from 1 to 4. The terms "halogen" or "halo" include fluorine, chlorine, bromine or iodine, most preferably fluorine or chlorine. The term "carboalkoxymethyl" refers to moieties having the general formula —$CH_2COOR_2$ in which $R_2$ is $C_1$–$C_4$ alkyl.

In the formula for the onium salts, the symbol $(R_3)_4$ indicates that four $C_1$–$C_8$ groups are present in the radicals; however, these alkyl groups may be identical or different.

The compounds of this invention, including the above intermediates, have been found to be active herbicides in possessing herbicidal activity against various species of weeds. In the broadest sense, the term "weeds" refers to plants which grow in locations in which they are not desired.

This invention also therefore relates to a method for controlling undesirable vegetation, comprising applying to a locus where control of such vegetation is desired, an herbicidally effective amount of a compound as described herein, and also relates to herbicidal compositions of matter comprising an herbicidally effective amount of a compound as described herein, together with an inert diluent or carrier suitable for use with herbicides.

As used herein the term "herbicide" refers to compounds which adversely control or modify the growth of plants, particularly of undesirable plants. By the term "herbicidally effective amount" is meant an amount of compound which causes an adverse controlling or modifying effect on the growth of plants. The term "plants" is meant to include germinant seeds, emerging seedlings, and established vegetation, including roots and above-ground portions. Such adverse modifying and controlling effects may include all deviations from natural development.

The compounds of this invention may be prepared by any of several general methods.

In one method (hereinafter Method A) the desired final product is prepared by reacting an onium salt as defined hereinabove with an appropriate amide according to the general reaction

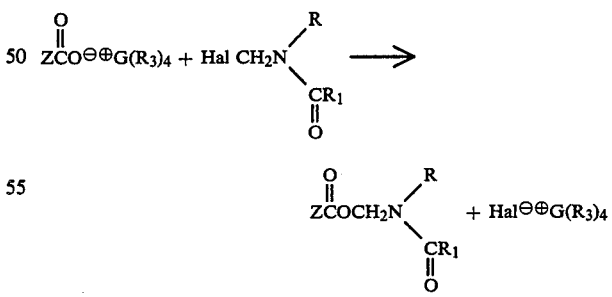

in which Z, R, $R_1$ and $R_3$ are as defined above and Hal is a halogen, preferably chlorine. Reactions of this type are most preferred in which onium salts of the type $Z'COO^\ominus \oplus G(R_3)_4$ are used, in which Z', $R_3$, and G are as defined previously.

Reactions of this type are generally carried out at temperatures of from about −25° C. to about 150° C., preferably from about 0° C. to about 80° C.

A solvent, particularly an aromatic solvent, may be used, but is not necessary. However, water must be excluded form the system during this reaction, so the solvent, if any, must be dry.

The intermediate onium salts are generally obtained by reaction of the appropriate carboxylic acid with a tetraalkyl onium salt according to the reaction

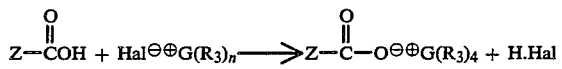

in which Z and $R_3$ are as defined above and Hal stands for a halogen. Such reactions are generally carried out at temperatures of about 0° C. to about 100° C., preferably from about 20° C. to about 25° C. in the presence of an aqueous base. The onium salts may be recovered by drying the product and distilling off the solvent.

The intermediate onium salts may contain four identical alkyl ($R_3$) groups or may be substituted by mixtures of $C_1$–$C_8$ alkyls.

The starting amides for the final step in the production of the desired compounds may be obtained, if not readily available, by reaction of an appropriate 1,3,5-trisubstituted-hexahydro-1,3,5-triazine with an acyl halide, analogously to the procedure described in U.S. Pat. No. 4,425,284. This procedure can be illustrated by the general reaction

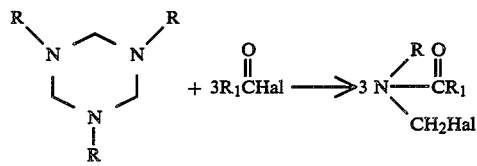

in which R and $R_1$ are as previously defined and Hal stands for halogen, preferably chlorine. Preferably this reaction is run at a temperature of from about 0° to about 120° C., more preferably from about 40° to about 100° C. and most preferably from about 75° to about 80° C. The reaction may be run at any convenient pressure, but is preferably performed at atmospheric pressure. A suitable inert solvent such as toluene, methylene chloride or ethylene dichloride is employed.

The following are examples of the preparation of compounds according to this invention.

EXAMPLE I

Preparation of
N-phenyl-N-[2-<4-(4'-trifluoromethyl)-phenoxy>-phenoxy]-propionoxymethyl chloroacetamide (Compound 1 herein)

(a) Preparation of intermediate amide.

In a flask were placed 21.9 milliliters (ml) (0.275 mol) chloroacetyl chloride and 500 ml of toluene. These were heated to reflux; then there was added, in small portions, 26.2 grams (g) (0.0833 mol) 1,3,5-triphenyl-hexahydro-1,3,5-triazine. The mixture was allowed to reflux for ½ hour after all the triazine had been added. The resulting mixture was then cooled, filtered, and solvents stripped off. There was obtained a nearly quantitative yield of the desired intermediate, N-phenyl-N-chloromethyl chloroacetamide.

(b) Preparation of intermediate onium salt.

In a flask, the following were introduced in this order: 24.5 g (0.306 mol) sodium hydroxide (as 50% aqueous solution), 50 g (0.153 mol) 2-[4-(4'trifluoromethyl)-phenoxy]phenoxy propionic acid, 200 ml water (with stirring), 250 ml methylene chloride and 51.9 g (0.153 mol) of tetra-(n-butyl) phosphonium bromide. The mixture was then stirred for 15 minutes; the layers were separated and the aqueous layer extracted twice with 250 ml portions of methylene chloride. The extracts were dried over magnesium sulfate and solvent stripped off.

The residue was extracted with 250 ml of benzene and the remaining water was separated by azeotropic distillation. There was obtained a nearly quantitative yield of the desired product, the tetrabutylphosphonium salt of the starting acid.

(c) The amide produced in step (a) was reacted with the onium salt of step (b) as follows:

In a flask there was placed 2.68 g (0.0046 mol) of the onium salt. Then, 1.0 g (0.0046 mol) of the amide of step (a), dissolved in benzene, was added dropwise at room temperature with good stirring. The stirring was continued 15 minutes after completion of addition. The solvent was stripped off, the product was extracted with diethyl ether, washed with water, dried and volatiles stripped off.

There was produced 1.4 g (60% of theoretical yield) of the desired product, $n_D^{30}$ 1.5388. The structure was confirmed by infrared, nuclear magnetic resonance and mass spectroscopy.

EXAMPLE 2

Production of
N-allyl-N-[2-<4-(4'-trifluoromethyl)phenoxy>-phenoxy]-propionoxy methyl dichloroacetamide (Compound 4 herein)

The intermediate amide, N-allyl, N-chloromethyl dichloroacetamide was prepared analogously to the procedure of Example 1(a) by reaction of dichloroacetyl chloride with 1,3,5-triallyl-hexahydro-1,3,5-triazine.

This amide (4.33 g, 0.02 mol) was reacted with 10.15 g (0.02 mol) of the tetrabutyl phosphonium salt prepared in Example 1(b), analogously to the procedure described in Example 1(c). There was produced 8.4 g (80% of theoretical yield) of the desired product, a waxy solid. The structure was confirmed by spectral analysis as in Example 1.

EXAMPLE 3

Preparation of
N-methyl-N-[2-<4-(4'-trifluoromethyl)-phenoxy>-phenoxy]propionoxy
methyl-2-nitro-5-(2-chloro-4-trifluoromethyl)phenoxy benzamide (Compound 6 herein)

(a) To a flask containing 10.4 g (0.0277 mol) of 5-[(2-chloro-4-trifluoromethyl)phenoxy]-2-nitrobenzoic acid, and one drop of pyridine in 20 ml of methylene chloride at room temperature there was added 5 ml of thionyl chloride. The mixture was stirred at room temperature for one hour, then heated to reflux, and subsequently evaporated to dryness under reduced pressure. The product was the acid chloride of the starting acid.

(b) The acid chloride produced in step (a) was added to 25 ml benzene and the mixture heated to reflux. To the refluxing mixture was added 1.24 g (0.0096 mol) of 1,3,5-trimethyl-hexahydro-1,3,5-triazine (dissolved in 5 ml benzene). The mixture was allowed to reflux.

(c) The following were combined in a flask in the order given: 15.29 g (0.19 mol) sodium hydroxide (as 50% aqueous solution); 34.34 g (0.095 mol) 2-nitro-5-[(2'-chloro-4'-trifluoromethyl)phenoxy]benzoic acid; 125 ml water; 150 ml methylene chloride; and 32.2 g (0.095 mol) of tetra-(n-butyl) phosphonium bromide. The combined mixture was stirred at room temperature for 15 minutes. The layers were separated and the aqueous layer extracted twice with methylene chloride. The extracts were combined with the organic phase which was then dried over anhydrous magnesium sulfate and evaporated under reduced pressure. The residue was dissolved in 250 ml benzene and the remaining water was removed by azeotropic distillation. There was obtained a nearly quantitative yield of the tetrabutyl phosphonium salt of the starting acid.

(d) In a flask there was placed 13.55 ml (0.0058 mol) of a 25% solution of the tetrabutyl phosphonium salt of step (c) in benzene. To this was added dropwise 2.45 g (0.0058 mol) of the amide produced in step (b), dissolved in 5 ml of benzene. The mixture was stirred at room temperature and heated at reflux for 15 minutes. The resulting mixture was washed with water, 5% potassium carbonate solution, dried over anhydrous magnesium sulfate and evaporated to dryness under reduced pressure. There was obtained 3.15 g of the desired product (76% of theoretical yield) $n_D^{30}$ 1.5394. The structure was confirmed by analysis as in Example 1.

The following Tables I and II depict representative compounds of this invention whose structures were similarly confirmed by spectral analyses.

TABLE I $$Z-\overset{O}{\underset{\|}{C}}OCH_2N\overset{R}{\underset{\underset{O}{\overset{\|}{C}}-R_1}{}}$$

| Cmpd. No. | R | $R_1$ | Z | $n_D^{30}$ |
|---|---|---|---|---|
| 1 |  | —CH$_2$Cl | 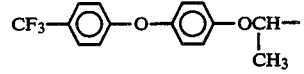 | 1.5388 |
| 2 | —CH$_3$ | —CH$_3$ | 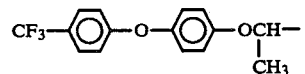 | 1.5124 |
| 3 | —CH$_2$COC$_2$H$_5$ (O) | —CH$_3$ | 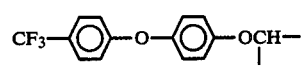 | 1.5108 |
| 4 | —CH$_2$CH=CH$_2$ | —CHCl$_2$ | 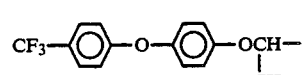 | waxy solid |
| 5 | —CH$_2$CN | —CH$_3$ | 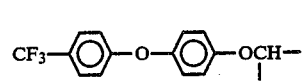 | 1.5145 |
| 6 | —CH$_3$ | 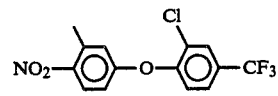 | 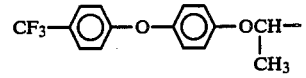 | 1.5394 |
| 7 | 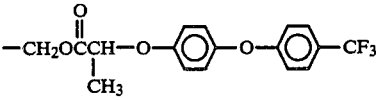 | H | 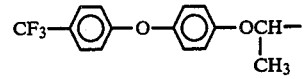 | 1.5394 |
| 8 | —CH$_2$CN | —CH$_3$ | 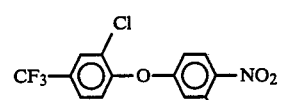 | 1.5365 |
| 9 | —CH$_2$CH=CH$_2$ | —CH$_3$ | 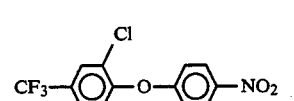 | 1.5283 |

TABLE I-continued $$Z-OCH_2N\begin{matrix}R\\|\\C-R_1\\||\\O\end{matrix}$$

(with Z—O—CO—CH$_2$—N group)

| Cmpd. No. | R | R$_1$ | Z | $n_D^{30}$ |
|---|---|---|---|---|
| 10 | —CH$_2$CH=CH$_2$ | —CHCl$_2$ | 2-chloro-4-(trifluoromethyl)phenoxy-3-methyl-4-nitrophenyl | 1.5430 |
| 11 | —CH$_2$—O—CO—(2-nitro-5-(2-chloro-4-trifluoromethylphenoxy)phenyl) | —H | 2-chloro-4-(trifluoromethyl)phenoxy-3-methyl-4-nitrophenyl | 1.5286 |
| 12 | —C$_6$H$_5$ | —CH$_3$ | 5-(trifluoromethyl)-2-pyridyloxy-phenyl-OCH(CH$_3$)— | 1.5393 |
| 13 | —CH$_2$COC$_2$H$_5$ | —CH$_3$ | 5-(trifluoromethyl)-2-pyridyloxy-phenyl-OCH(CH$_3$)— | 1.5016 |
| 14 | —CH$_2$CH=CH$_2$ | —CH$_3$ | 5-(trifluoromethyl)-2-pyridyloxy-phenyl-OCH(CH$_3$)— | 1.5120 |
| 15 | 3-(trifluoromethyl)phenyl | —CH$_3$ | 5-(trifluoromethyl)-2-pyridyloxy-phenyl-OCH(CH$_3$)— | waxy solid |
| 16 | —CH$_2$CN | —CH$_3$ | 5-(trifluoromethyl)-2-pyridyloxy-phenyl-OCH(CH$_3$)— | 1.5137 |
| 17 | —CH$_3$ | —CH$_3$ | 5-(trifluoromethyl)-2-pyridyloxy-phenyl-OCH(CH$_3$)— | 1.5102 |
| 18 | —CH(CH$_3$)$_2$ | —CH$_3$ | 2,4-dichlorophenoxy-CH$_2$— | 1.5050 |
| 19 | —CH$_3$ | —CH$_3$ | 2,4-dichlorophenoxy-CH$_2$— | m.p. 86–90° C. |

TABLE II $$Z'-\overset{O}{\underset{\|}{C}}O^{\ominus}{}^{\oplus}G(R_3)_4$$

| Cmpd. No. | n | R₃ | G | Z' | $n_D^{30}$ |
|---|---|---|---|---|---|
| 20 | 4 | n-C₄H₉ | P | CF₃—(pyridyl)—O—(phenyl)—OCH(CH₃)— | 1.5095 |
| 21 | 4 | n-C₄H₉ | P | CF₃—(phenyl)—O—(phenyl)—OCH(CH₃)— | 1.5136 |
| 22 | 4 | n-C₄H₉ | P | CF₃—(phenyl, Cl)—O—(phenyl)—NO₂ | 1.5217 |

The compounds listed in the foregoing Tables I and II were tested for herbicidal activity as follows:

Pre-Emergence Herbicide Screening Test

Flats were filled with sandy loam soil containing a fungicide and fertilizer. The soil was leveled and rows of three grassy weeds, four broadleaf weeds and yellow nutsedge (*Cyperus esculentus*), were planted thickly enough so that several seedlings emerged per inch of row. The grassy weeds were: foxtail (Setaria spp.), watergrass (*Echinochloa crusgalli*) and wild oat (*Avena fatua*). Broadleaf weeds utilized were annual morning-glory (*Ipomoea purpurea*), velvetleaf (*Alutilon theophrasti*), mustard (*Brassica juncea*), and curly dock (*Rumex crispus*).

The flats were placed in a greenhouse at 70°–85° F. and watered by sprinkling. One day after planting the flats were sprayed with a solution of a test compound at a rate of 80 gallons of solution per acre with the compound being applied at a rate of 4 pounds per acre (4.48 kg/ha).

The solutions of the test compounds were made by weighing out 300 mg of the compound in question into a 120 ml wide-mouth bottle, dissolving it in 50 ml of acetone containing 1% polyoxyethylene sorbitan monolaurate emulsifier and then diluting to 100 ml with water. Additional solvents, not exceeding 5 ml, were used if needed to dissolve the compound.

The flats were returned to the greenhouse after spraying and watered daily by sprinkling. The degree of weed control was estimated and recorded 3 weeks after treatment, as percentage control compared to the growth of the same species in an untreated check flat of the same age.

The percent control is based on the total injury to the plants due to all factors, including inhibited germination, killing of the plant tissue after emergence, stunting, malformation, chlorosis, and other types of injury. The control ratings vary from 0 to 100 percent, where 0 represents no effect with growth equal to the untreated control, and 100 represents complete kill.

Post-Emergence Herbicidal Evaluation

The soil was prepared and seeded with the same varieties as described for the pre-emergence test. The flats were placed in the greenhouse at 70°–85° F. and watered by sprinkling. Nine to eleven days after planting, the flats were sprayed on a table at a rate of 80 gallons of solution per acre. The compound was applied at the rate of 4 pounds/acre (4.48 kg/ha). The spray solution was made up similarly to that described for the pre-emergence evaluation.

The flats were returned to the greenhouse after spraying and watered daily without wetting the foliage for three days. Thereafter, they were watered daily by sprinkling. Three weeks after treatment the degree of weed control was estimated and recorded as percentage control compared to the growth of the same species in an untreated check flat of the same age. The percent control ratings were assigned on the same basis as for the pre-emergence evaluation.

The following Table II contains the results of these tests, in terms of average control of the three grasses, four broadleaf weeds, and yellow nutsedge, respectively, in both pre- and post-emergence evaluations.

TABLE III

| Compound Number | Pre-Emergence Control | | | Post-Emergence control | | |
|---|---|---|---|---|---|---|
| | grasses | broadleaf weeds | nutsedge | grasses | broadleaf weeds | nutsedge |
| 1 | 93 | 13 | 20 | 93 | 25 | 0 |
| 2 | 100 | 0 | 0 | 100 | 0 | 0 |
| 3 | 100 | 10 | 30 | 100 | 10 | 0 |
| 4 | 100 | 0 | 0 | 100 | 0 | 0 |
| 5 | 98 | 0 | 0 | 100 | 0 | 0 |
| 6 | 70 | 68 | 20 | 83 | 98 | 0 |
| 7 | 100 | 0 | 0 | 100 | 30 | 0 |
| 8 | 90 | 93 | 50 | 97 | 100 | 60 |
| 9 | 98 | 95 | 30 | 100 | 100 | 80 |
| 10 | 80 | 90 | 20 | 90 | 100 | 50 |
| 11 | 83 | 70 | 30 | 97 | 100 | 50 |
| 12 | 97 | 0 | 0 | 100 | 0 | 0 |
| 13 | 100 | 0 | 0 | 100 | 0 | 0 |
| 14 | 100 | 0 | 0 | 100 | 0 | 0 |
| 15 | 100 | 0 | 0 | 100 | 0 | 0 |
| 16 | 100 | 0 | 0 | 100 | 0 | 0 |
| 17 | 100 | 0 | 0 | 100 | 0 | 0 |
| 18 | 63 | 98 | 40 | 30 | 100 | 30 |

TABLE III-continued

| Compound Number | Pre-Emergence Control | | | Post-Emergence control | | |
|---|---|---|---|---|---|---|
| | grasses | broadleaf weeds | nut-sedge | grasses | broadleaf weeds | nut-sedge |
| 19 | 71 | 61 | 0 | 70 | 100 | 90 |
| 20 | 100 | 0 | 0 | 100 | 0 | 0 |
| 21 | 99 | 0 | 0 | 100 | 6 | 0 |
| 22 | 98 | 100 | 80 | 97 | 100 | 80 | included were: soybean (*Glycine max*), rice (*Oryza sativa*), cotton (*Gossypium herbaceum*), corn (*Zea mays*), wheat (*Triticum aestivum*), milo (*Sorghum vulgare*) and sugarbeets (*Beta vulgaris*).

The following Table IV contains the results of these tests, in terms of average control of the six broadleaf weeds, six grassy weeds, and nutsedge, and injury to the crop species, with visual ratings ranging from 0% (no injury) to 100% (complete kill) as compared to untreated control flats.

TABLE IV

| Cmpd. No. | lb/A | Broadleaf weeds | grasses | nut-sedge | soybean | corn | rice | cotton | wheat | milo | Sugarbeets |
|---|---|---|---|---|---|---|---|---|---|---|---|
| 1 | 1.00 | — | 100 | 0 | 0 | 97 | 100 | 0 | 100 | 100 | 0 |
| 1 | 0.50 | — | 93 | 0 | 0 | 85 | 97 | 0 | 100 | 100 | 0 |
| 1 | 0.25 | — | 77 | 0 | 0 | 15 | 60 | 0 | 95 | 100 | 0 |
| 2 | 2.00 | 0 | 100 | 0 | 25 | 100 | 100 | 0 | 100 | 100 | 0 |
| 2 | 1.00 | — | 99 | 0 | 10 | 100 | 100 | 0 | 100 | 100 | 0 |
| 2 | 0.50 | — | 90 | 0 | 0 | 90 | 97 | 0 | 90 | 97 | 0 |
| 2 | 0.25 | — | 90 | 0 | 0 | 35 | 90 | 0 | 85 | 95 | 0 |
| 2 | 0.01 | — | 37 | 0 | 0 | 20 | 15 | 0 | 20 | 80 | 0 |
| 4 | 2.00 | 0 | 100 | 0 | 0 | 100 | 100 | 0 | 95 | 100 | 0 |
| 4 | 1.00 | — | 92 | 0 | 0 | 90 | 100 | 0 | 95 | 100 | 0 |
| 4 | 0.50 | — | 86 | 0 | 0 | 20 | 70 | 0 | 35 | 95 | 0 |
| 4 | 0.25 | — | 41 | 0 | 0 | 20 | 40 | 0 | 10 | 80 | 0 |
| 4 | 0.01 | — | 19 | 0 | 0 | 0 | 0 | 0 | 0 | 80 | 0 |
| 5 | 2.00 | 12 | 99 | 0 | 35 | 98 | 100 | 0 | 85 | 100 | 0 |
| 5 | 1.00 | — | 97 | 0 | 15 | 90 | 95 | 0 | 45 | 100 | 0 |
| 6 | 2.00 | 76 | 86 | 25 | 0 | 90 | 97 | 0 | 60 | 100 | 100 |
| 6 | 0.50 | 37 | — | 15 | 0 | 20 | 70 | 0 | 0 | 80 | 60 |
| 9 | 2.00 | 80 | 88 | 60 | 0 | 65 | 60 | 95 | 50 | 100 | 0 |
| 9 | 0.50 | 26 | 49 | 45 | 0 | 40 | 40 | 40 | 50 | 90 | 0 |
| 10 | 2.00 | 91 | 86 | 70 | 0 | 75 | 70 | 65 | 60 | 100 | 100 |
| 10 | 0.50 | 27 | 58 | 40 | 0 | 30 | 60 | 35 | 15 | 100 | 100 |
| 11 | 2.00 | 92 | 86 | 60 | 0 | 70 | 75 | 85 | 70 | 100 | 100 |
| 11 | 0.50 | 67 | 54 | 40 | 0 | 35 | 65 | 10 | 30 | 100 | 100 |
| 19 | 2.00 | 69 | 33 | 0 | 85 | 25 | 75 | 85 | 40 | 40 | 85 |
| 19 | 1.00 | 59 | 19 | 0 | 60 | 0 | 40 | 10 | 0 | 30 | 10 |
| 21 | 2.00 | 0 | 96 | 0 | 0 | 97 | 100 | 15 | 90 | 100 | 0 |
| 21 | 0.50 | — | 90 | 0 | 0 | 15 | 70 | 15 | 75 | 97 | 0 |
| 21 | 0.25 | — | 71 | 0 | 0 | 20 | 60 | 0 | 25 | 97 | 0 |
| 21 | 0.01 | — | 26 | 0 | 0 | 10 | 15 | 0 | 0 | 25 | 0 |
| 22 | 2.00 | 99 | 91 | 60 | 0 | 70 | 75 | 65 | 80 | 100 | 100 |
| 22 | 1.00 | 81 | 62 | 55 | 0 | 60 | 70 | 30 | 65 | 100 | 100 |
| 22 | 0.50 | 74 | 51 | 30 | 0 | 20 | 25 | 20 | 15 | 100 | 100 |
| 22 | 0.25 | 31 | 34 | 0 | 0 | 15 | 15 | 0 | 0 | 90 | 70 |

Pre-Emergence multi-weed/multi-crop evaluation

Selection compounds from Tables I and II were variously evaluated at application rates of 0.01, 0.25, 0.5, 1.0 and 2.0 pounds active ingredient/acre (0.0112, 0.28, 0.56, 1.12 and 2.24 kg/ha, respectively) for pre-emergence activity against a number of weed and crop species. The procedure was generally similar to the pre-emergence evaluation described above. Weed species utilized were as follows: grassy weeds—downy brome (*Bromus tectorum*), foxtail (*Setaria* sp), annual ryegrass (*Lolium multiflorum*), watergrass (*Echinochloa crusgalli*), shattercane (*Sorghum bicolor*), wild oats (*Avena fatua*); broadleaf weeds—signalgrass (*Brachiaria platyphylla*), annual morningglory (*Ipomoea purpurea*), sesbania (*Sesbania* sp.), velvetleaf (*Abutilon theophrasti*), sicklepod (*Cassia obtusifolia*) and mustard (Brassica sp.). Yellow nutsedge was also included in these tests. Crops Post-Emergence Multi-weed/Multi-crop Evaluation Selected compounds from Tables I and II were variously evaluated at application rates of 0.1, 0.25, 0.5, 110 and 2.0 pounds active ingredient/acre (0.112, 0.28, 0.56, 1.12 and 2.24 kg/ha, respectively) for post-emergence activity against a number of weed and crop species. The procedure was generally similar to the pre-emergence evaluation described above; the same weed and crop species were utilized.

The following Table V contains the results of these tests, in terms of average control of the six broadleaf weeds, six grassy weeds, and nutsedge, and injury to the crop species, with visual ratings ranging from 0% (no injury) to 100% (complete kill) as compared to untreated control flats.

TABLE V

| Cmpd. No. | lb/A | Broadleaf weeds | grasses | nut-sedge | soybean | corn | rice | cotton | wheat | milo | Sugarbeets |
|---|---|---|---|---|---|---|---|---|---|---|---|
| 1 | 1.00 | — | 81 | 0 | 0 | 100 | 85 | 0 | 45 | 95 | 0 |
| 1 | 0.50 | — | 79 | 0 | 0 | 97 | 75 | 0 | 45 | 95 | 0 |
| 2 | 2.00 | 0 | 100 | 0 | 20 | 100 | 100 | 10 | 100 | 100 | 0 |
| 2 | 1.00 | — | 100 | 0 | 0 | 100 | 95 | 10 | 100 | 100 | 0 |
| 2 | 0.50 | — | 91 | 0 | 0 | 100 | 95 | 10 | 100 | 100 | 0 |

TABLE V-continued

| Cmpd. No. | lb/A | Broad-leaf weeds | grasses | nut-sedge | soy-bean | corn | rice | cotton | wheat | milo | Sugar-beets |
|---|---|---|---|---|---|---|---|---|---|---|---|
| 2 | 0.25 | — | 80 | 0 | 0 | 100 | 90 | 0 | 98 | 100 | 0 |
| 2 | 0.10 | — | 51 | 0 | 0 | 100 | 10 | 0 | 75 | 100 | 0 |
| 4 | 2.00 | 0 | 100 | 0 | 25 | 100 | 100 | 35 | 100 | 100 | 0 |
| 4 | 1.00 | — | 100 | 0 | 0 | 100 | 90 | 0 | 100 | 100 | 0 |
| 4 | 0.50 | — | 88 | 0 | 0 | 100 | 90 | 0 | 100 | 100 | 0 |
| 4 | 0.25 | — | 63 | 0 | 0 | 100 | 80 | 0 | 75 | 100 | 0 |
| 4 | 0.10 | — | 46 | 0 | 0 | 95 | 35 | 0 | 70 | 100 | 0 |
| 5 | 2.00 | 0 | 100 | 0 | 40 | 100 | 95 | 0 | 90 | 100 | 0 |
| 5 | 1.00 | 0 | 100 | 0 | 40 | 85 | 85 | 0 | 80 | 100 | 0 |
| 5 | 0.50 | — | 90 | 0 | 35 | 85 | 60 | 0 | 45 | 70 | 0 |
| 6 | 2.0 | 85 | 100 | 60 | 50 | 100 | 70 | 100 | 100 | 100 | 100 |
| 6 | 0.25 | 56 | 56 | 0 | 10 | 100 | 10 | 60 | 60 | 75 | 100 |
| 6 | 0.10 | 48 | — | 0 | 15 | 25 | 0 | 60 | 10 | 20 | 70 |
| 9 | 2.00 | 86 | 51 | 0 | 15 | 15 | 45 | 60 | 60 | 75 | 100 |
| 9 | 0.25 | 69 | 23 | 0 | 15 | 15 | 20 | 60 | 10 | 70 | 100 |
| 10 | 2.00 | 100 | 62 | 65 | 50 | 60 | 60 | 100 | 70 | 100 | 100 |
| 10 | 0.25 | 93 | 33 | 0 | 15 | 10 | 10 | 90 | 30 | 75 | 100 |
| 10 | 0.10 | 77 | — | 0 | 15 | 15 | 0 | 80 | 0 | 75 | 90 |
| 11 | 2.00 | 98 | 74 | 60 | 40 | 100 | 70 | 100 | 70 | 90 | 100 |
| 11 | 0.25 | 71 | 36 | 20 | 40 | 97 | 40 | 95 | 30 | 95 | 100 |
| 11 | 0.10 | 51 | — | 0 | 0 | 70 | 0 | 90 | 0 | 95 | 100 |
| 19 | 2.00 | 89 | 0 | 15 | 100 | 30 | 23 | 90 | 25 | 40 | 85 |
| 19 | 1.00 | 83 | 0 | 0 | 98 | 15 | 15 | 85 | 20 | 30 | 60 |
| 19 | 0.50 | 74 | — | 0 | 70 | 10 | 10 | 80 | 20 | 20 | 40 |
| 19 | 0.25 | 47 | — | 0 | 70 | 0 | 10 | 50 | 20 | 10 | 35 |
| 21 | 2.00 | 6 | 100 | 0 | 15 | 100 | 100 | 15 | 100 | 100 | 0 |
| 21 | 0.50 | — | 92 | 0 | 0 | 95 | 50 | 15 | 100 | 100 | 0 |
| 21 | 0.25 | — | 63 | 0 | 0 | 70 | 50 | 10 | 75 | 95 | 0 |
| 21 | 0.10 | — | 24 | 0 | 10 | 70 | 10 | 10 | 15 | 60 | 0 |
| 21 | 0.05 | — | 14 | 0 | 0 | 65 | 0 | 10 | 15 | 60 | 0 |
| 22 | 2.00 | 99 | 56 | 80 | 40 | 45 | 60 | 100 | 50 | 100 | 100 |
| 22 | 1.00 | 82 | 31 | 35 | 40 | 25 | 60 | 80 | 40 | 90 | 65 |
| 22 | 0.50 | 76 | 19 | 0 | 35 | 10 | 10 | 35 | 20 | 60 | 50 |
| 22 | 0.25 | 55 | 12 | 0 | 10 | 0 | 10 | 30 | 0 | 35 | 50 |

In the tests reported in Tables IV and V, some compounds were also tested for activity, both pre-emergent and post-emergent against cocklebur (*Xanthium pennsylvanicum*). Compounds 6, 9, 11 and 19 showed good control of this weed; Compounds 2, 4, 5, and 21 showed little or no control.

In practice, a pure compound can be used as a herbicide. However, in general, the compounds are first formulated with one or more inert carriers or diluents suitable for herbicidal use, before being applied.

The compositions or formulations, including a compound as described herein, may exist in any one of a number of solid or liquid forms. Examples of solid forms are dusts, granules, tablets, powders and the like. Examples of liquid forms are emulsifiable concentrates, flowables and pastes. Such compositions may contain, in addition to the active compound or compounds, various carriers or diluents; surface active agents (wetting agents, dispersing agents and/or emulsifying agents); solvents (water, or organic solvents such as aromatic solvents or chlorinated aliphatic solvents); adhesives; thickeners; binders; antifoaming agents; and other substances as mentioned herein. Solid carriers or diluents included in such compositions or formulations may include, for example, ground natural minerals such as kaolins, alumina, calcium carbonate, silica, kieselguhr, clay, etc.; ground synthetic minerals such as various silicates and aluminosilicates and ground vegetable products such as bark, cornmeal, sawdust, cellulose powder and the like.

To manufacture solid compositions, the active substances are mixed with solid carriers or diluents such as those mentioned above and the mixture is ground to the appropriate size. Granules can be manufactured by dissolving an active compound in an organic solvent and applying the mixture, for example, by atomization, onto an absorptive granulated inert material, such as silica. Adhesives may be utilized to assist in the incorporation of the compound onto the solid particles.

Wettable powders, flowables, and pastes are obtained by mixing and grinding an active compound with one or more dispersing agents and/or solid carriers or diluents. Also included may be wetting agents and/or dispersing agents, for example, lignins, methyl cellulose, naphthalenesulfonic acid derivatives, fatty alcohol sulfates and various types of alkali and alkaline earth metal salts of fatty acids.

Emulsifiable concentrates are generally obtained by dissolving the active compound in an organic solvent, for example, butanol, cyclohexanone, xylenes, or higher boiling aromatic hydrocarbons. To obtain suspensions or emulsions in water, wetting agents are generally also added.

It is possible to use highly concentrated liquid compositions containing up to about 95% by weight of the active compound, or even the active compound alone for those compounds which are liquids, when applying the compound in the form of a finely divided liquid by use of various atomizing equipment, for example by airplane crop spraying techniques. For other purposes, however, the various types of compositions which can be utilized for these compounds will contain varying amounts of the compound according to the type of composition and the intended use.

In general, compositions may contain from 0.1 to 95% of the active compound, more preferably from 0.5 to 90%. Some typical compositions will contain an active compound as follows: wettable powders, flowables and pastes—20 to 90% active compound; oil suspensions, emulsions, solutions and emulsifiable concentrates—5 to 90% active compound; aqueous suspensions—10 to 50% active compound; dusts and powders—1 to 25% active compound; granules and pellets—1 to 20% active compound.

The rate of application of the active compound to a locus to be controlled will depend on the nature of the seeds and plants to be controlled and will vary from about 0.05 to about 50 pounds per acre (about 0.06 to about 56 kg/ha).

In addition to the active compound and the various agents utilized in preparing compositions and formulations mentioned above, such compositions may also contain one or more other active compounds of the type mentioned herein as well as other pesticidal agents, such as herbicides, fungicides, insecticides, acaricides, nematocides, bactericides, and plant growth regulators. Such compositions may also contain soil disinfectants or fumigants and may further contain fertilizers, thus making it possible to provide multi-purpose compositions containing one or more of the compounds described herein as well as, optionally, other pesticides and also fertilizers, all intended and formulated for use at the same locus.

Compositions containing one or more of the active compounds decsribed, in a herbicidally effective amount, may be applied to the plant or locus to be controlled in any conventional manner. Thus, powders and various liquid compositions containing the active compound can be applied by the use of power dusters, boom and hand sprayers and spray dusters, or applied from airplanes as mists or sprays. When applied in the latter method they may be effective in very low dosages. To modify or control growth of germinating seeds or emerging seedlings liquid compositions may be applied to the soil with conventional methods and may be distributed in the soil to a depth of one-half inch below the soil surface. The compositions need not be admixed with the soil particles but can be applied merely by sprinkling on the surface of the soil.

Compositions including active compounds may also be applied by addition to irrigation waters supplied to the field to be treated. This method of application permits penetration of the compounds into the soil as the water is absorbed therein.

| EXAMPLES OF TYPICAL COMPOSITIONS | |
|---|---|
| Ingredient | Weight % |
| Oil | |
| Compound 1 | 1 |
| Oil solvent-heavy aromatic naphtha | 99 |
| Total | 100 |
| Emulsifiable Concentrate | |
| Compound 2 | 50 |
| Kerosene | 45 |
| Emulsifying agent (mixture of long chain ethoxylated polyethers with long chain sulfonate) | 5 |
| Total | 100 |
| Emulsifiable Concentrate | |
| Compound 3 | 90 |
| Kerosene | 5 |
| Emulsifying agent (mixture of long chain ethoxylated polyethers with long chain sulfonate) | 5 |
| Total | 100 |
| Dusts and/or Powders | |
| Ingredient | Wt. % | Wt. % | Wt. % |
| Compound 4 | 0.5 | 50.0 | 90.0 |

-continued

| EXAMPLES OF TYPICAL COMPOSITIONS | | | |
|---|---|---|---|
| Attapulgite Clay Powder | 93.5 | 44.0 | 4.0 |
| Sodium lignin sulfonate | 5.0 | 5.0 | 5.0 |
| Sodium dioctyl sulfosuccinate | 1.0 | 1.0 | 1.0 |
| Total | 100.0 | 100.0 | 100.0 |

What is claimed is:

1. Compounds having the formula

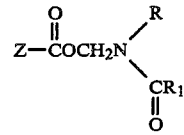

in which Z is

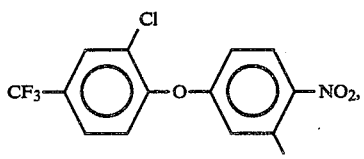

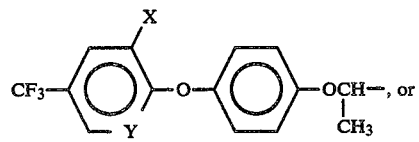

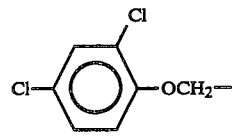

wherein X is hydrogen or halogen and Y is —CH or N; R is alkyl, phenyl, trihalomethylphenyl, cyanomethyl, carboalkoxymethyl,

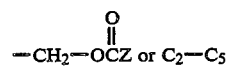

alkenyl; and $R_1$ is hydrogen, lower alkyl, halo-(lower alkyl), or Z.

2. A compound according to claim 1 in which R is $C_1$-$C_6$ alkyl.

3. A compound according to claim 1 in which Z is

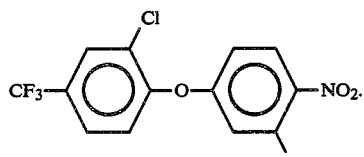

4. A compound according to claim 3 in which R is cyanomethyl and $R_1$ is methyl.

5. A compound according to claim 3 in which R is allyl and $R_1$ is methyl.

6. A compound according to claim 3 in which R is allyl and $R_1$ is chloromethyl.

7. A compound according to claim 3 in which R is

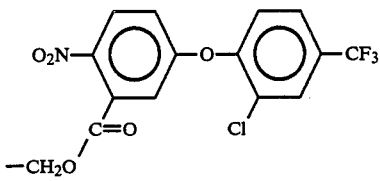

and R₁ is hydrogen.

8. A compound according to claim 1 in which Z is

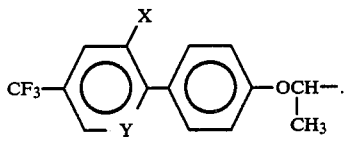

9. A compound according to claim 8 in which Y is —CH, X is hydrogen, R is phenyl and R₁ is chloromethyl.

10. A compound according to claim 8 in which Y is —CH, X is hydrogen and R and R₁ are both methyl.

11. A compound according to claim 8 in which Y is —CH, X is hydrogen, R is carboethoxymethyl and R₁ is methyl.

12. A compound according to claim 8 in which Y is —CH, X is hydrogen, R is allyl and R₁ is dichloromethyl.

13. A compound according to claim 8 in which Y is —CH, X is hydrogen, R is cyanomethyl and R₁ is methyl.

14. A compound according to claim 8 in which Y is —CH, X is hydrogen, R is methyl and R₁ is

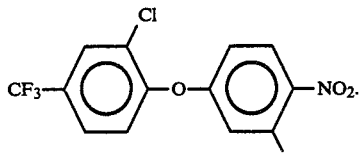

15. A compound according to claim 8 in which Y is —CH, X is hydrogen, R is

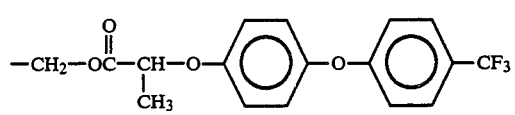

and R₁ is hydrogen.

16. A compound according to claim 8 in which Y is N, X is hydrogen, R is phenyl and R₁ is methyl.

17. A compound according to claim 8 in which Y is N, X is hydrogen, R is carboethoxymethyl and R₁ is methyl.

18. A compound according to claim 8 in which Y is N, X is hydrogen, R is allyl and R₁ is methyl.

19. A compound according to claim 8 in which Y is N, X is hydrogen, R is 3-trifluoromethylphenyl and R₁ is methyl.

20. A compound according to claim 8 in which Y is N, X is hydrogen, R is cyanomethyl and R₁ is methyl.

21. A compound according to claim 8 in which Y is N, X is hydrogen and R and R₁ are both methyl.

22. A compound according to claim 1 in which Z is

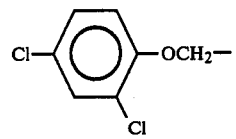

23. A compound according to claim 22 in which R is isopropyl and R₁ is methyl.

24. A compound according to claim 22 in which R and R₁ are both methyl.

25. A method for controlling undesirable vegetation comprising applying to said vegetation or the locus thereof an herbicidally effective amount of a compound according to claim 1.

26. An herbicidal composition comprising: (a) an herbicidally effective amount of a compound according to claim 1; and (b) an herbicidally suitable diluent or carrier.

27. A compound having the formula

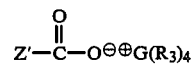

in which Z' is

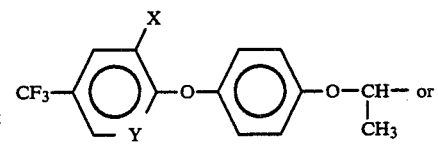

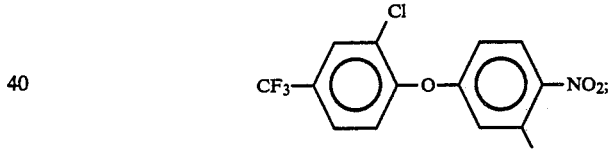

G is nitrogen or phosphorus; R₃ is C₁–C₈ alkyl, X is hydrogen or halogen; and Y is —CH or N.

28. A compound according to claim 27 in which Z' is

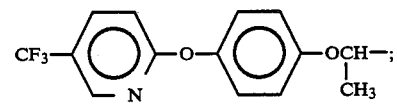

G is phosphorus and R₃ is n-butyl.

29. A compound according to claim 27 in which Z' is

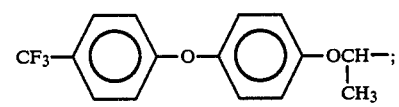

G is phosphorus and R₃ is n-butyl.

30. A compound according to claim 27 in which Z' is

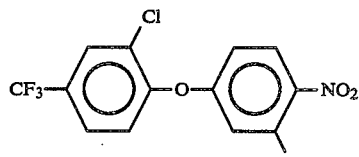

G is phosphorus and $R_3$ is n-butyl.

31. A method of controlling undesirable vegetation comprising applying to said vegetation or the locus thereof an herbicidally effective amount of a compound according to claim 27.

32. An herbicidal composition of matter comprising: (a) an herbicidally effective amount of a compound according to claim 27; and (b) an herbicidally suitable inert diluent or carrier.

* * * * *